United States Patent [19]
Lincoln et al.

[11] Patent Number: 5,762,876
[45] Date of Patent: Jun. 9, 1998

US005762876A

[54] AUTOMATIC GENOTYPE DETERMINATION

[75] Inventors: Stephen E. Lincoln, Cockeysville; Michael R. Knapp, Baltimore, both of Md.

[73] Assignee: Molecular Tool, Inc., Baltimore, Md.

[21] Appl. No.: 362,266

[22] Filed: Dec. 22, 1994

Related U.S. Application Data

[63] Continuation-in-part of Ser. No. 173,173, Dec. 23, 1993, abandoned, and a continuation-in-part of Ser. No. 775,786, Oct. 11, 1991, which is a continuation-in-part of Ser. No. 664,837, Mar. 5, 1991, said Ser. No. 173,173, is a continuation-in-part of Ser. No. 162,397, Dec. 6, 1993, abandoned, Ser. No. 155,746, Nov. 23, 1993, Pat. No. 5,518,900, and Ser. No. 145,145, Nov. 3, 1993, abandoned.

[51] Int. Cl.⁶ .......... G01N 21/29; G01N 21/41; G01N 21/47; G01N 21/00
[52] U.S. Cl. .......... 422/67; 422/82.08; 422/82.09; 422/82.05; 435/6; 935/87; 436/50
[58] Field of Search .......... 422/82.05, 82.08, 422/82.09, 67; 435/6; 935/87; 436/50

[56] References Cited

U.S. PATENT DOCUMENTS

| | | | |
|---|---|---|---|
| 4,309,112 | 1/1982 | Ashley et al. | 422/82.09 |
| 4,852,017 | 7/1989 | Hunkapiller | 364/497 |
| 5,221,518 | 6/1993 | Mills | 422/82.05 |
| 5,415,839 | 5/1995 | Zaun et al. | 422/82.05 |
| 5,443,791 | 8/1995 | Cathcort et al. | 422/65 |
| 5,449,621 | 9/1995 | Klein | 422/82.09 |
| 5,453,247 | 9/1995 | Beavis et al. | 422/68.1 |

FOREIGN PATENT DOCUMENTS

| | | |
|---|---|---|
| 8803957 | 6/1988 | WIPO |
| 9215712 WOA92 15712 | 9/1992 | WIPO |
| WOA93 11262 | 6/1993 | WIPO |

OTHER PUBLICATIONS

Fisher Scientific Catalog, p. 697, (1983).

Theo T. Nikiforov, Robert B. Rendle, Philip Goelet, Yu-Hui Rogers, Michael L. Kotewicz, Stephen Anderson, George L. Trainor, and Michael R. Knapp, *Genetic Bit Analysis: a solid phase method for typing single nucleotide polymorphisms*, Nucleic Acid Research, 1994, vol. 22, No. 20, pp. 4167-4175.

Balding, David J., Torney, David, C., *Statistical Analysis of DNA Fingerprint Data for Ordered Clone Physical Mapping of Human Chromosomes*, Bulletin of Mathematical Biology, 1991, vol. 53, No. 6, pp. 853-879.

Mark Keatin, M.D., *Linkage Analysis and Long QT Syndrome Using Genetings to Study Cardiovascular Disease*, Research Advance Series, Focus on Molecular Biology, vol. 85, No. 6, Jun., 1992, pp. 1973-1986.

*Primary Examiner*—Paul B. Prebilic
*Attorney, Agent, or Firm*—Bromberg & Sunstein LLP

[57] ABSTRACT

A device determines the genotype at selected loci within genetic material obtained from a biological sample. One or more data sets are formed and a set of probability distributions including at least one distribution is established. These distributions associate hypothetical reaction values with corresponding probabilities for each genotype of interest at the same locus or at different loci. The genotype is then determined based on these measures.

14 Claims, 6 Drawing Sheets

| LOCUS# | SUBJECT# | X-VALUE | Y-VALUE | GENOTYPE | CONFIDENCE |
|---|---|---|---|---|---|
| 177 | 213-a01 | 0.176 | 1.688 | TT | 8.15 |
| 177 | 213-a02 | 0.11 | 2.303 | TT | 9.41 |
| 177 | 213-a03 | 0.399 | 0.575 | CT | 2.93 |
| 177 | 213-a04 | 1.02 | 1.492 | CT | 9.85 |
| 177 | 213-a05 | 0.971 | 1.557 | CT | 9.99 |
| 177 | 213-a06 | 0.91 | 1.513 | CT | 10 |
| 177 | 213-a07 | 0.165 | 1.604 | TT | 8.33 |
| 177 | 213-a08 | 1.168 | 0.173 | CC | 8.33 |
| 177 | 213-a09 | 0.158 | 1.573 | TT | 8.47 |
| 177 | 213-a10 | 1.429 | 0.046 | CC | 9.44 |
| 177 | 213-a11 | 1.365 | 0.047 | CC | 9.46 |
| 177 | 213-a12 | 0.186 | 0.35 | NS | 1.93 |
| 177 | 213-b01 | 0.367 | 0.302 | CT | 0.03 |
| 177 | 213-b02 | 0.193 | 2.019 | TT | 8.03 |
| 177 | 213-b03 | 0.138 | 2.039 | TT | 8.97 |
| 177 | 213-b04 | 0.913 | 1.618 | CT | 9.99 |
| 177 | 213-b05 | 0.152 | 2.111 | TT | 8.74 |
| 177 | 213-b06 | 0.308 | 0.261 | NS | 1.2 |
| 177 | 213-b07 | 0.234 | 1.825 | TT | 7.14 |
| 177 | 213-b08 | 0.787 | 1.321 | CT | 10 |
| 177 | 213-b09 | 0.746 | 1.481 | CT | 9.73 |
| 177 | 213-b10 | 1.018 | 1.423 | CT | 9.72 |
| 177 | 213-b11 | 0.897 | 1.775 | CT | 9.83 |
| 177 | 213-b12 | 1.223 | 0.054 | CC | 9.44 |
| 177 | 213-c01 | 0.308 | 0.513 | CT | 0.91 |
| 177 | 213-c02 | 1.594 | 0.061 | CC | 9.29 |
| 177 | 213-c03 | 1.487 | 0.046 | CC | 9.42 |
| 177 | 213-c04 | 0.191 | 1.998 | TT | 8.05 |
| 177 | 213-C05 | 1.395 | 0.053 | CC | 9.4 |
| 177 | 213-c06 | 0.8 | 1.551 | CT | 9.79 |
| 177 | 213-c07 | 0.244 | 1.973 | TT | 7.08 |
| 177 | 213-c08 | 0.504 | 0.706 | CT | 4.46 |
| 177 | 213-c09 | 0.243 | 1.977 | TT | 7.11 |
| 177 | 213-c10 | 0.96 | 1.831 | CT | 9.94 |
| 177 | 213-c11 | 1.43 | 0.068 | CC | 9.27 |
| 177 | 213-c12 | 0.824 | 1.369 | CT | 10 |

FIG.8

AUTOMATIC GENOTYPE DETERMINATION

CROSS REFERENCE TO RELATED APPLICATIONS

This application is a continuation in part of application Ser. No. 08/173,173, filed Dec. 23, 1993 now abandoned, which is for an invention entitled "Automatic Genotype Determination," by Stephen E. Lincoln and Michael P. Knapp. This immediate parent application is a continuation in part of application Ser. No. 07/775,786, filed Oct. 11, 1991, for an invention entitled "Nucleic Acid Typing by Polymerase Extension of Oligonucleotides using Terminator Mixtures," by P. Goelet, M. Knapp, and S. Anderson, which in turn is a continuation in part of application Ser. No. 07/664,837, filed Mar. 5, 1991. Immediate parent application Ser. No. 08/173,173 is also a continuation in part of application Ser. No. 08/162,397, filed Dec. 6, 1993 now abandoned, for an invention entitled "Method for Immobilization of Nucleic Acid Molecules" by T. Nikiforov and M. Knapp, and of application Ser. No. 08/155,746, filed Nov. 23, 1993 issued May 21, 1996 as U.S. Pat. No. 5,518,900, for an invention entitled "Method for Generating Single-Stranded DNA Molecules" by T. Nikiforov and M. Knapp, and of application Ser. No. 08/145,145, filed Nov. 3, 1993 now abandoned, for an invention entitled "Single Nucleotide Polymorphisms and their use in Genetic Analysis" by M. Knapp and P. Goelet. All of these related applications are hereby incorporated herein by reference.

TECHNICAL FIELD

The present invention relates to the methods and devices for determining the genotype at a locus within genetic material.

SUMMARY OF THE INVENTION

The present invention provides in one embodiment a method of determining the genotype at a locus within genetic material obtained from a biological sample. In accordance with this method, the material is reacted at the locus to produce a first reaction value indicative of the presence of a given allele at the locus. There is formed a data set including the first reaction value. There is also established a set of one or more probability distributions; these distributions associate hypothetical reaction values with corresponding probabilities for each genotype of interest at the locus. The first reaction value is applied to each probability distribution to determine a measure of the conditional probability of each genotype of interest at the locus. The genotype is then determined based on these measures.

In accordance with a further embodiment of this method, the material at the locus is subject to a second reaction to produce a second reaction value independently indicative of the presence of a second allele at the locus. A second data set is formed and the second reaction value is included in the second data set. Each probability distribution associates a hypothetical pair of first and second reaction values with a single probability of each genotype of interest. The first data set includes other reaction values obtained under conditions comparable to those under which the first reaction value was produced, and the second data set includes other reaction values obtained under conditions comparable to those under which the second reaction value was produced. Where, for example, there are two alleles of interest, the first reaction may be an assay for one allele and the second reaction may be a distinct assay for the other allele. The first and second data sets may include reaction values for the first and second reactions respectively, run under comparable conditions on other samples with respect to the same locus. Alternatively, or in addition, the data sets may include reaction values for reactions run under comparable conditions with respect to different loci within the same sample.

In accordance with a further embodiment, the probability distributions may be determined iteratively. In this embodiment, each probability distribution is initially estimated. Each initial probability distribution is used to determine initial genotype probabilities using the reaction values in the data sets. The resulting data are then used to modify the initial probability distribution, so that the modified distribution more accurately reflects the reaction values in the data set. This procedure may be iterated a desired number of times to improve the probability distribution. In practice, we have generally found that a single iteration is sufficient.

The foregoing methods have been employed with success for automatic genotype determination based on assays using genetic bit analysis (GBA). In such a case, each allele may typically be a single specific nucleotide. In accordance with GBA, a reaction is designed to produce a value that is indicative of the presence of a specific allele at the locus within the genetic material. In GBA, the approach is typically to hybridize a specific oligonucleotide to the genetic material at the locus immediately adjacent to the nucleotide being interrogated. Next, DNA polymerase is applied in the presence of differentially labelled dideoxynucleoside triphosphates. The read-out steps detect the presence of one or more of the labels which have become covalently attached to the 3' end of the oligonucleotide. Details are provided in Theo R. Nikiforov et al. "Genetic Bit Analysis, a solid phase method for typing single nucleotide polymorphisms," 22 *Nucleic Acids Research*, No. 20, 4167–4175 (1994), which is hereby incorporated herein by reference. However, the present invention is also applicable to other reaction systems for allele determination, such as allele-specific hybridization (ASH), sequencing by hybridization (CBH), oligonucleotide ligase assay (OLA), and allele-specific amplification, using either the ligase chain reaction (LCR) or the polymerase chain reactions (PCR). The alleles assayed may be defined, for example, by a single nucleotide, a pair of nucleotides, a restriction site, or (at least in part) by its length in nucleotides.

In another embodiment of the invention, there is provided a method of determining the genotype of a subject by reacting genetic material taken from the subject at selected loci. In this embodiment, each locus may be an identified single nucleotide or group of nucleotides, and there is produced with respect to each of the selected loci a reaction value indicative of the presence of a given allele at each of the selected loci. These reaction values are used to determine the genotype of the subject or alternatively a DNA sequence associated with a specific region of genetic material of the subject. (Indeed a set of genotypes for selected proximal loci may be used to specify a sequence of the genetic material.) In further embodiments, the loci are selected to provide one or more types of information concerning the subject, including inheritance of a trait, parentage, identity, and matching tissue with that of a donor. Alternatively, the loci may be spaced throughout the entire genome of subject to assist in characterizing the genome of the species of the subject.

In a further embodiment of the invention, there is provided a device for determining the genotype at a locus within genetic material obtained from a subject. The device of this embodiment has a reaction value generation arrangement for producing a first physical state, quantifiable as a first reaction value, indicative of the presence of a given allele at the locus, the value associated with reaction of the material at the locus. The device also has a storage arrangement for storing a data set including the first reaction value and other reaction values obtained under comparable conditions. A distribution establishment arrangement establishes a set of probability distributions, including at least one distribution, associating hypothetical reaction values with corresponding probabilities for each genotype of interest at the locus. A genotype calculation arrangement applies the first reaction value to each pertinent probability distribution to determine the conditional probability of each genotype of interest at the locus. A genotype determination arrangement determines the genotype based on data from the genotype calculation arrangement.

In a further embodiment, the device may determine the genotype at selected loci. In this embodiment, the reaction generation arrangement can produce a reaction value indicative of the presence of a given allele at each of the selected loci and the data set includes reaction values obtained with respect to each of the selected loci. The genotype calculation arrangement applies reaction values obtained with respect to each of the selected loci to each pertinent probability distribution.

In another further embodiment, the device may determine the genotype at a locus within genetic material from each of a plurality of samples. In this embodiment, the reaction generation arrangement can produce a reaction value indicative of the presence of a given allele at the locus of material obtained from each sample and the data set includes reaction values obtained with respect to each sample. The genotype calculation arrangement applies reaction values obtained with respect to each sample to each pertinent probability distribution.

In each of these embodiments the reaction value generation arrangement may also include an arrangement for producing a second reaction value, independently indicative of the presence of a second allele at the locus. The storage arrangement then includes a provision for storing the second reaction value and other reaction values obtained under comparable conditions. The genotype calculation arrangement applies the first and second reaction values to each pertinent probability distribution to determine the probability of each genotype of interest at the locus. Each probability distribution may be of the type associating a hypothetical pair of first and second reaction values with a single probability of each genotype of interest. The locus may be a single nucleotide, and the reaction value generation arrangement may include an optical transducer to read reaction results and may determine, on a substantially concurrent basis, the reaction values with respect to each sample.

The distribution establishment arrangement may be configured to assign a initial probability distribution to the data set that would associate hypothetical reaction values with corresponding probabilities for each genotype of interest at the locus. The distribution establishment arrangement then invokes the genotype calculation means to use each initial probability distribution to determine initial conditional probabilities for a genotype of interest at the locus. Thereafter the distribution establishment arrangement modifies each initial probability distribution, so that each modified distribution more accurately reflects the reaction values stored in the storage means.

The term "reaction value" as used in this description and the following claims may refer either to a single numerical value or to a collection of numbers associated with a physical state produced by the reaction. In the GBA method described in the Nikiforov article referred to above, e.g., optical signals are produced that may be read as a single numerical value. Alternatively, e.g., an optical signal may be simplified over time, and the reaction value may be the collection of samples of such a signal. It is also possible to form a scanned image, of one or a series of optical signals generated by GBA or other reaction methods, and to digitize this image, so that a collection of pixel values in all or a portion of the image constitutes a reaction value.

BRIEF DESCRIPTION OF THE DRAWINGS

The foregoing aspects of the invention will be more readily understood by reference to the following detailed description, taken with respect to the following drawings, in which:

FIG. 8 is an example of the output of the device in FIG. 1.

DETAILED DESCRIPTION OF SPECIFIC EMBODIMENTS

The invention provides in preferred embodiments a method and device for genotype determination using genetic marker systems that produce allele-specific quantitative signals. An embodiment uses computer processing, employing computer software we developed and call "GetGenos", of data produced by a device we also developed to produce GBA data. The device achieves, among other things, the following:

Fully automatic genotype determination from quantitative data. Off-line analysis of data pools is intended, although the software is fast enough to use interactively.

Ability to examine many allele tests per DNA sample simultaneously. One genotype and confidence measure are produced from these data.

A true probabilistic confidence measure (a LOD score), properly calibrated, is produced for each genotype.

Use of robust statistical methods: Noise reduction via selective data pooling and simultaneous search over points in a data pool, preventing bias.

Maximal avoidance of arbitrary parameters, and thus insensitivity to great variation in input data. The small number of parameters that are required by the underlying statistical model are fit to the observed data, essentially using the data set as its own internal control.

Flexibility for handling multiple data types. Essentially, only probability distribution calculations, described below, need to be calibrated to new data types. We expect that the invention may be applied to GBA, OLA, ASH, and RAPD-type markers.

Our current embodiment of the software is implemented in portable ANSI C, for easy integration into a custom laboratory information system. This code has been successfully run on:

Macintosh
Sun
MS-DOS
MS-Windows

In our current embodiment of the software, a number of consistency checks are performed for GBA data verification, using both the raw GBA values and the control wells. Overall statistics for trend analysis and QC are computed. Brief "Genotype Reports" are generated, summarizing results for each data set, including failures. All data are output in a convenient form for import into interactive statistical packages, such as DataDesk™. The current implementation is presently restricted to 2-allele tests in diploids—the situation with present GBA applications.

Figure 1:
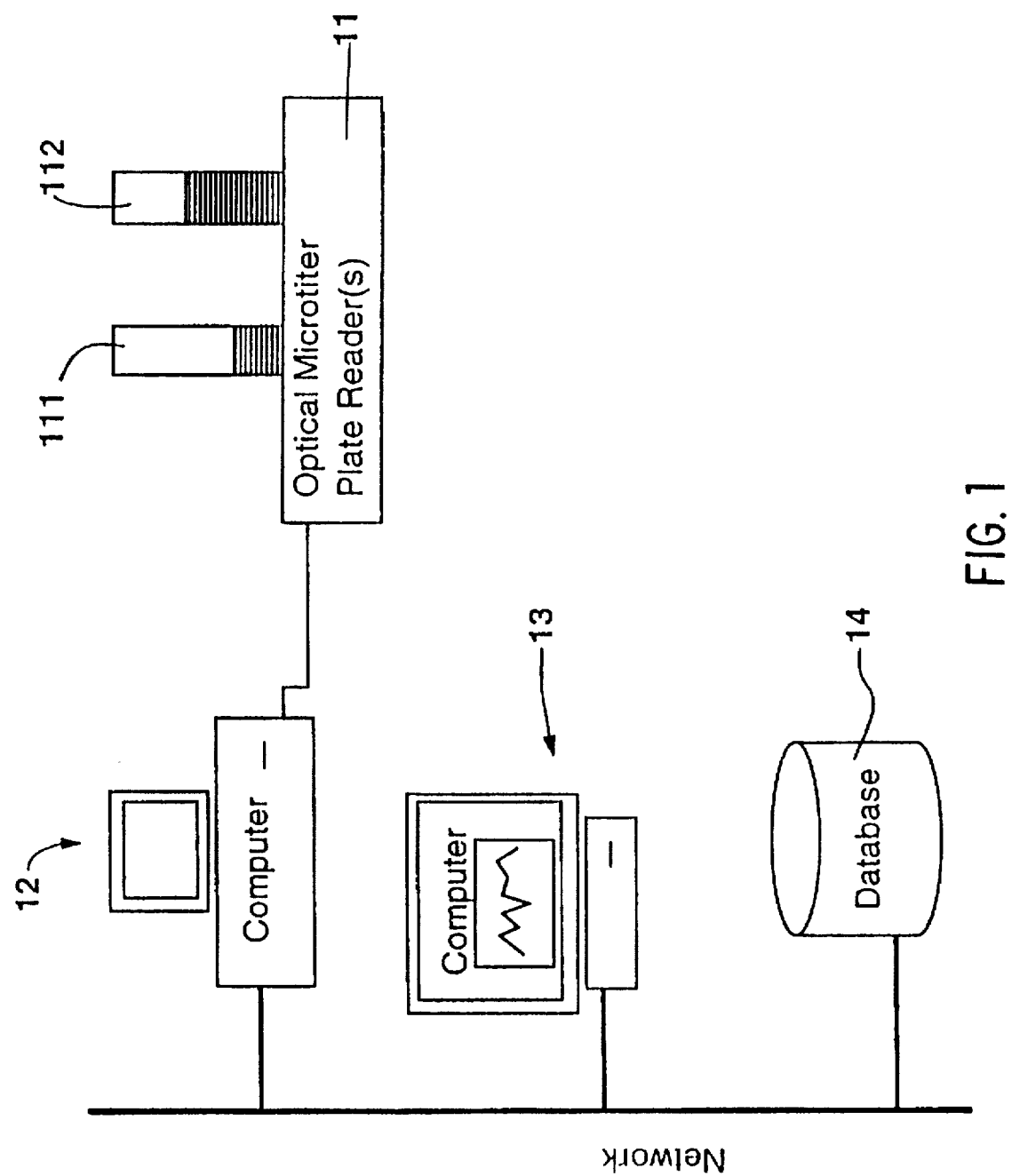
FIG. 1 is a diagram of a device in accordance with a preferred embodiment of the invention.

Referring to FIG. 1, there is shown a preferred embodiment of a device in accordance with the present invention. The device includes an optical detector 11 to produce reaction values resulting from one or more reactions. These reactions assay for one or more alleles in samples of genetic material. We have implemented the detector 11 using bichromatic microplate reader model 348 and microplate stacker model 83 from ICN Biomedical, Inc., P.O. Box 5023, Costa Mesa, Calif. 92626. The microplates are in a 96 well format, and the reader accommodates 20 microplates in a single processing batch. Accordingly the device of this embodence permits large batch processing. The reactions in our implementation use GBA, as described above. The detector 11 is controlled by computer 12 to cause selected readout of reaction values from each well. The computer 12 is programmed to allow for multiple readout of the reaction value from a given well over a period of time. The values are stored temporarily in memory and then saved in database 14. Computer 13 accesses the database 14 over line 15 and processes the data in accordance with the procedure described below. Of course, computers 12 and 13 and database 14 may be implemented by a integral controller and data storage arrangement. Such an arrangement could in fact be located in the housing of the optical detector 11.

Figure 2:
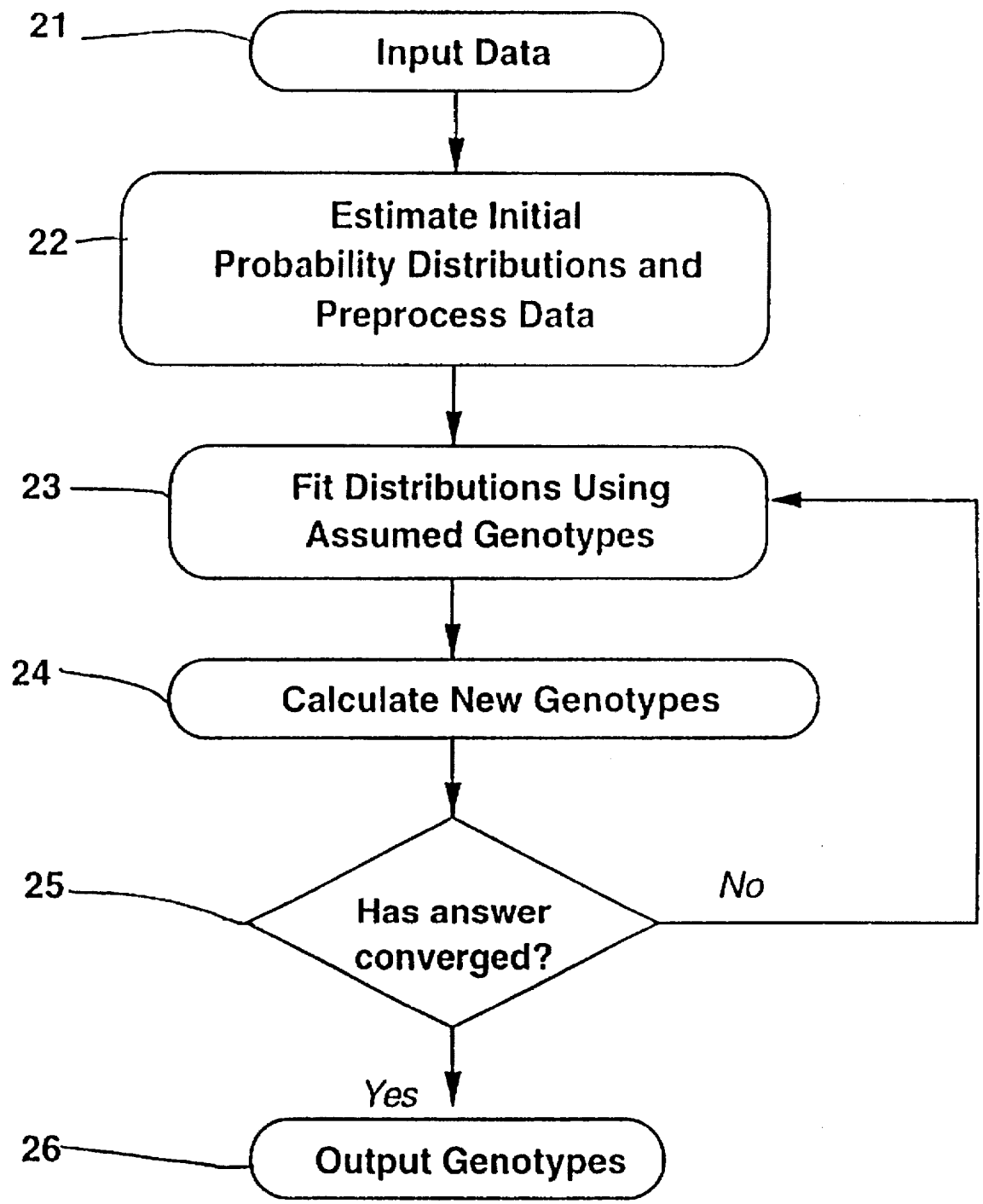
FIG. 2 is a diagram of the logical flow in accordance with the embodiment of FIG. 1.

In FIG. 2 is shown the procedure followed by computer 13. The steps of this procedure are as follows.

Input Data

A set of data is loaded under step 21. In most applications, each experiment in the set should be testing (i) the same genetic marker, and (ii) the same set of alleles of that marker, using comparable biochemistry (e.g. the same reagent batches, etc.). Large data sets help smooth out noise, although the appropriate size of a data set depends on the allele frequencies (and thus the number of expected individuals of each genotypic class). Each data point in the input data may be thought of as an N-tuple of numeric values, where N is the number of signals collected from each DNA sample for this locus. (N will usually be the number of alleles tested at this marker, denoted A, except when repeated testing is used, in which case N may be greater than A).

Preprocess Data

Next the data are subject to preprocessing (step 22). An internal M-dimensional Euclidean representation of the input signals is produced, where each input datum (an N-tuple) is a point in M-space. Usually, M will be the same as N and the coordinates of the point will be the values of the input tuple, and thus the preprocessing will be trivial (although see the first paragraph of variations discussed). The Euclidean space may be non-linear, depending on the best available models of signal generation. (Completely mathematically equivalently, any non-linearity may be embodied in the initial probability distributions, described below.)

Figure 3:
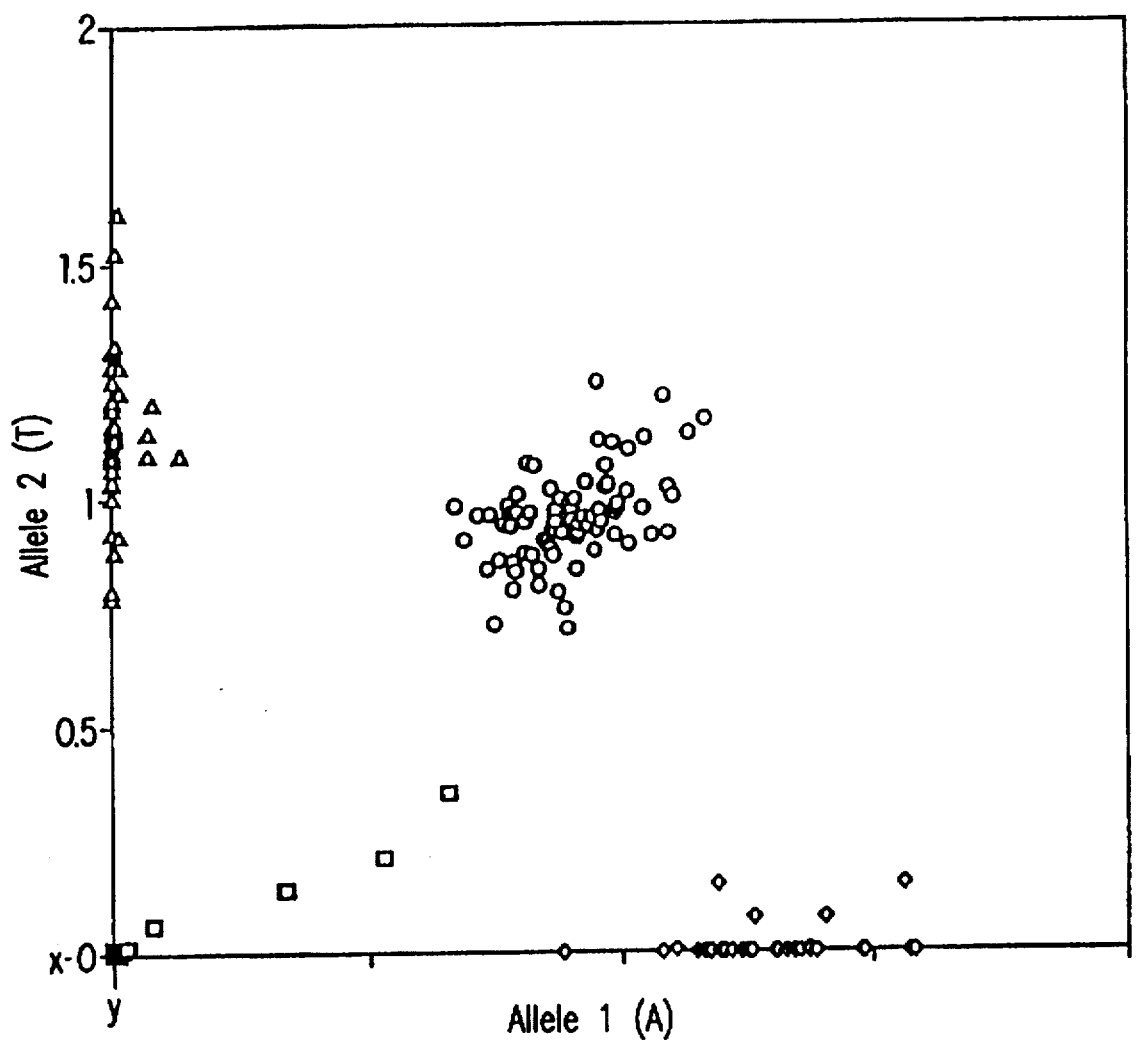
FIG. 3 is a graph of numeric reaction values (data) generated by the embodiment of FIG. 1 as well as the genotype determinations made by the embodiment from these data.
Figure 4:
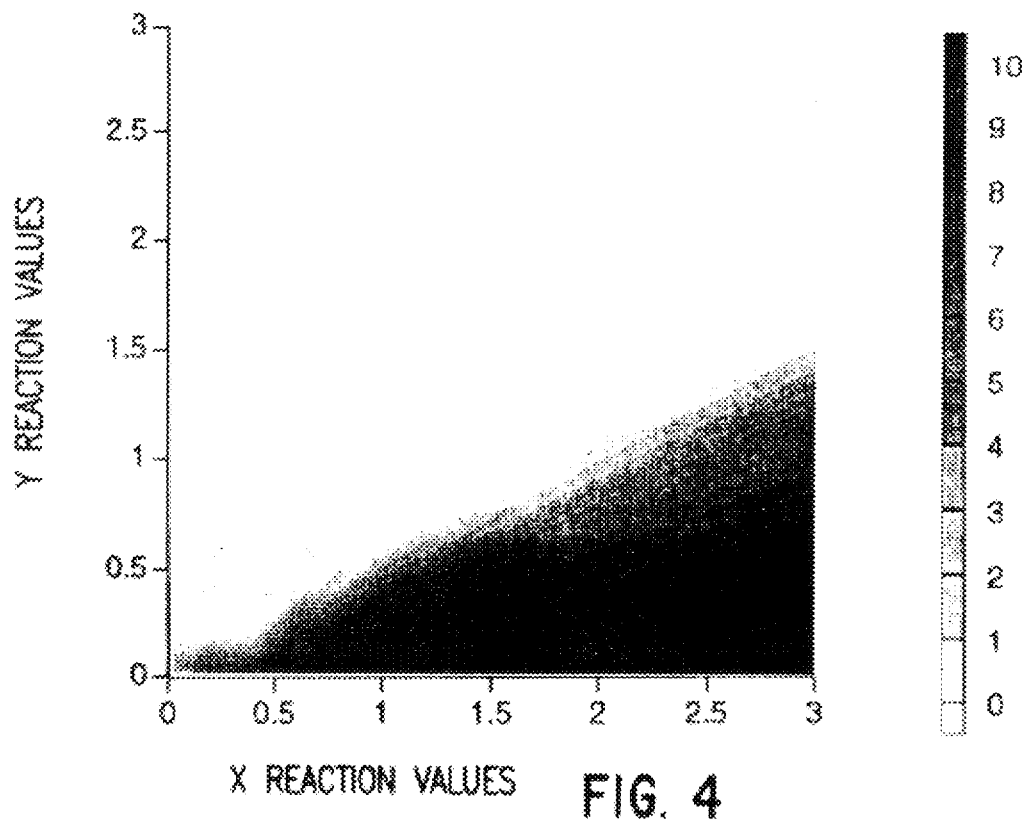
FIGS. 4–7 respectively show probability distributions derived by the embodiment of FIG. 1 for three genotypes of interest (AA, AT, and TT) and a failure mode at a locus.
Figure 5:
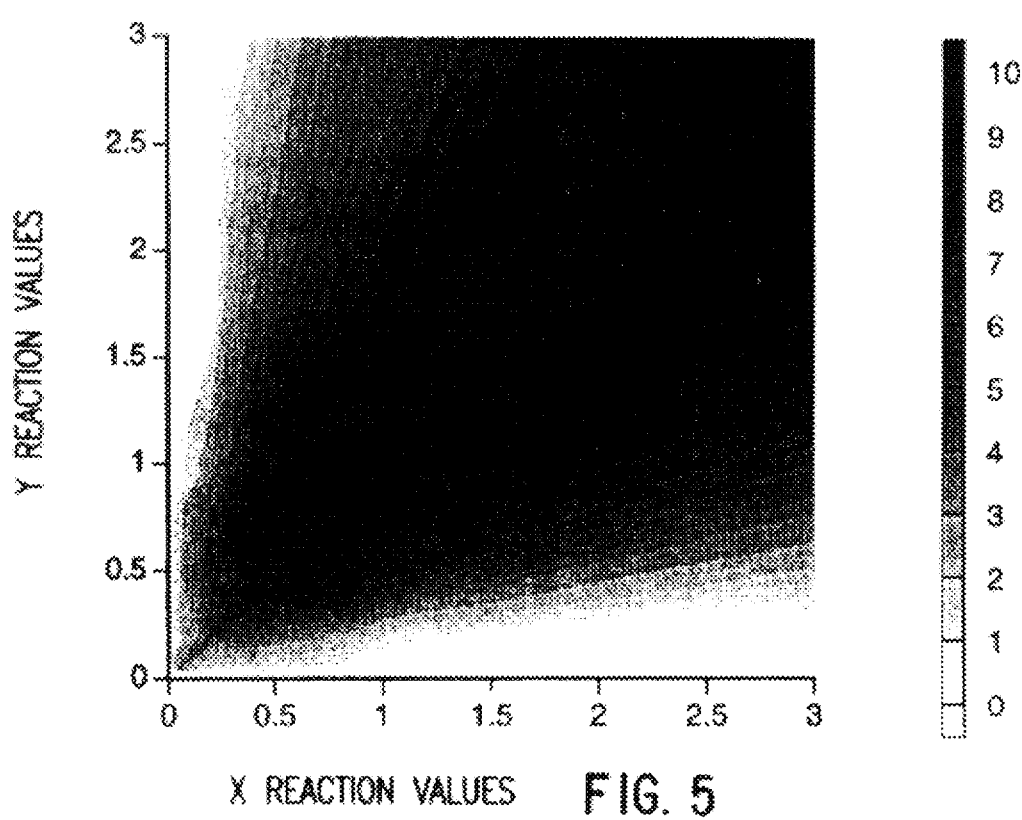
Figure 6:
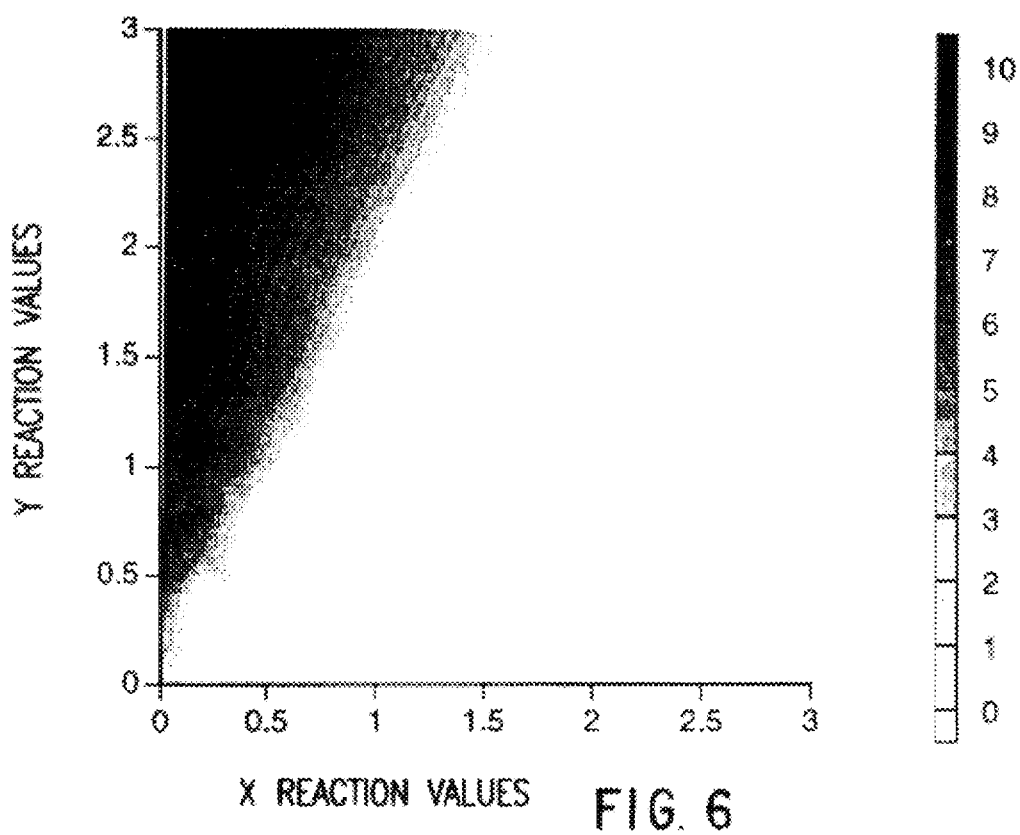
Figure 7:
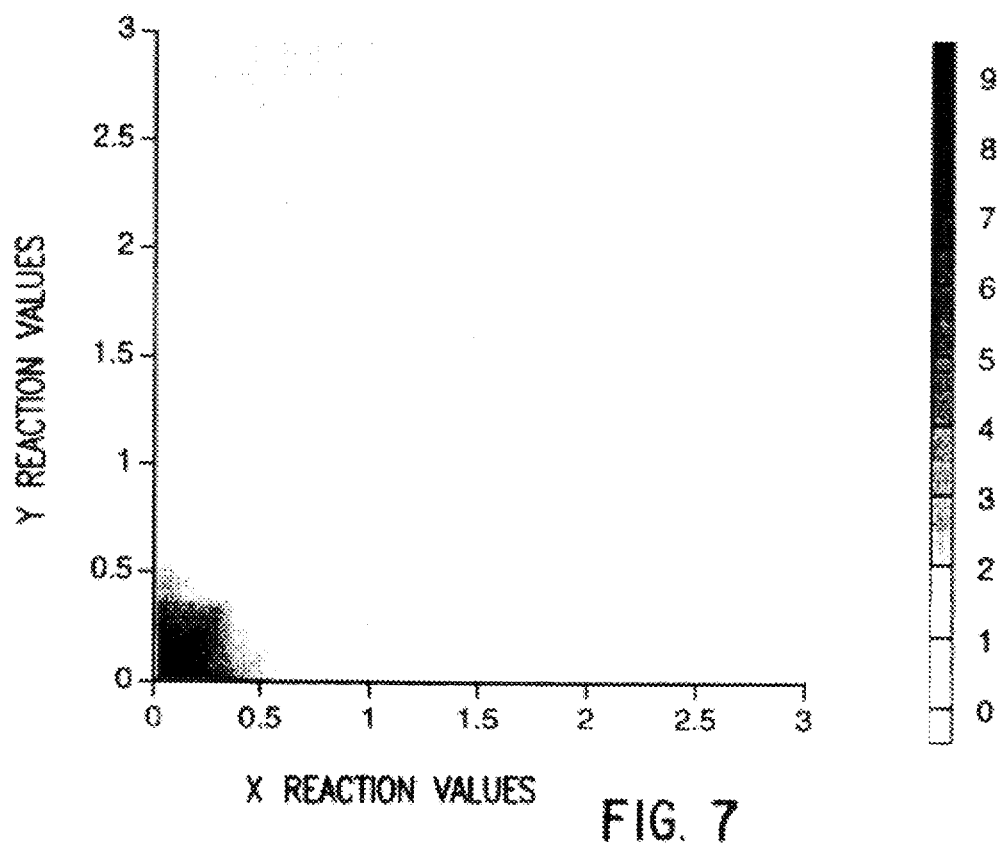

FIG. 3 illustrates preprocessed reaction values from step 22 for GBA locus 177-2 on 80 DNA samples. The X-axis indicates preprocessed reaction values for allele 1 (A) and the Y-axis indicates preprocessed reaction values for allele 2 (T). For clarity, the results of genotype determination are also indicated for each point: Triangles are TT genotype, diamonds are AA, circles are AT, and squares are failures (no signal).

Probability Distributions

Returning to FIG. 2, under step 22, initial probability distributions are established for the G possible genotypes. For example, in a random diploid population containing A tested alleles:

$$G = (A) + (A-1) + \ldots + 1 = \frac{A(A+1)}{2} \tag{1}$$

The initial conditional probability for any hypothetical input datum (a point in M-space, denoted $X_i$) and genotype (denoted g) is defined as the prior probability of seeing the signal $X_i$ assuming that g is the correct genotype of that datum. That is:

$Pr(\text{signal } X_i \mid \text{Genotype}=g)$, where $X_i=(x_i^1 \ldots x_i^M)$ and $g \in \{1 \ldots G\}$ \hfill (2)

FIGS. 4 through 7 illustrate the initial probability distributions established for the data in FIG. 3. Probability distributions are indicated for the four genotypic classes of interest, AA, AT, TT and No Signal, in FIGS. 4, 5, 6, and 7 respectively. The shading at each XY position indicates probability, with darker shades indicating increased probability for hypothetical data points with those X and Y reaction valves.

Exactly where these distributions come from is highly specific to the nature of the input data. The probability distributions can either be pre-computed at this step and stored as quantized data, or can be calculated on the fly as needed in step 23, below. The probability distributions may be fixed, or may be fit to the observed data or may be fit to assumed genotypes as determined by previous iterations of this algorithm. (See Additional Features below.)

Under step 23, we compute the conditional probability of each genotype. For each datum $X_i$, the above probabilities are collected into an overall conditional posterior probability of each genotype for that datum:

$Pr(\text{Genotype} = g | \text{Signal} X_i) =$ \hfill (3)

$$\frac{Pr(\text{Signal } X_i | \text{Genotype} = g) \cdot Pr(\text{Genotype} = g)}{Pr(\text{Signal } X_i)}$$

where

Pr(Genotype=g) is the prior probability of any datum having genotype g;

Pr(Signal $X_i$) is the prior probability of the signal (a constant which may be ignored); and Pr(Signal $X_i$|Genotype=g) is the initial probability defined above.

Under step 24, we determine the select the genotype and compute the confidence score. For each datum, using the above posterior probabilities, we determine the most likely genotype assignment g' (the genotype with the highest posterior probability) and its confidence score. The confidence score C is simply the log of the odds ratio:

$$C = \log_{10} \frac{Pr(\text{Genotype} = g'|\text{Signal } X_i)}{\sum_{\text{Genotypes } g} Pr(\text{Genotype} = g|\text{Signal } X_i)} \quad (4)$$

It should be noted that this procedure is significant, among other reasons, because it permits determining a robust probabalistic confidence score associated with each geno type determination.

Under step 25, there may be employed adaptive fitting. A classic iterative adaptive fitting algorithm, such as Estimation-Maximization (E-M), may be used to increase the ability to deal with highly different input data sets and reduce noise sensitivity. In this case, the genotypes computed in step 24 are used to refit the distributions (from step 22). In step 25, a convergence test is performed, which may cause the program to loop back to step 23, but now using the new distributions.

As one example, an E-M search procedure may be used to maximize the total likelihood, that is, to find the maximally likely set of genotype assignments given the input data set. (The net likelihood may be calculated from the Baysean probabilities, defined above.) For appropriate likelihood calculations and probability distributions, the EM principle will guarantee that this algorithm always produces true maximum-likelihood values, regardless of initial guess, and that it always converges.

Output Data: Under step 26, we output the results (genotypes and confidence scores) to the user or to a computer database. An example of such output is shown in FIG. 8.

Additional Features

Additional features may be incorporated into the above procedure. They may be integrated into the procedure either together or separately, and have all been implemented in a preferred embodiment.

Preprocessing: During steps 21 or 22, the data (either input tuples or spatial data points) may be preprocessed in order to reduce noise, using any one of many classical statistical or signal-processing techniques. Control data points may be used in this step. In fact, various types of signal filtering or normalizing may be applied at almost any step in the algorithm.

Fitting Probability Distributions: The probability distributions calculated in steps 22 and 23 may be fit to the input data—that is, each distribution may be a function of values which are in part calculated from the input data. For example, we may define the conditional probability of a signal point for some genotype to be a function of the distance between that point and the observed mean for that signal.

Using an Initial Genotype Guess: In step 22, either a simple or heuristic algorithm may be used to produce a initial genotype guess for each input data point. If a fairly accurate guess can be produced, then the probability distributions for each genotype may be fit to the subset of the data assumed to be of that genotypic class. Another use of a genotype guess is in initial input validity checks and/or preprocessing (e.g. Step 22), before the remainder of the algorithm is applied. To be useful, a guess need not produce complete genotypic information, however.

Using a Null Genotypic Class: In steps 22 and all further steps, one (or more) additional probability distributions may be added to fit the data to the signals one would expect to see if an experiment (e.g. that datum) failed. E.g., $$Pr(\text{signal } X_i | \text{Genotype} \notin \{1 \ldots G\})$$

The current implementation above is presently restricted to M=2 and N=2*R, where R is the number of repeated tests of both alleles. We refer to the two alleles as X and Y. The program understands the notion of "plates" of data, a number of which make up a data set.

The Initial Guess Variation is employed to initially fit distributions using the heuristic described below. The Initial Guess is produced during the Preprocessing Step which normalizes and background subtracts the input data, and remove apparent outlier points as well. These steps are performed separately for each allele's signal (i.e., 1 dimensional analysis). In fact, this preprocessing is applied separately to each of the R repeated tests, and the test with the small total 2 dimension residual is chosen for use in further steps. Various other preprocessing and post-processing steps are employed for GBA data validation and QC. In particular, controls producing a known reaction value may be employed to assure integrity of the biochemical process. In a preferred embodiment, signals are assumed to be small positive numbers (between 0.0 and 5.0, with 0.0 indicating that allele is likely not present in the sample, and larger values indicating that it may be.

To handle a wide range of input data signal strengths, the Adaptive Fitting Variation is employed. However, the program is hard-coded to perform exactly one or two interactions passes through step 25, which we find works well for existing GBA data.

The probability distributions we fit at present in steps 22 and 25 have as their only parameters (i) the ratio of the X and Y signals for heterozygotes, and (ii) the variance from the normalized means (0.0 negative for that allele, 1.0 for positive for that allele) along each axis separately. In fact, these later numbers are constrained to be at least a fixed minimum, which is rarely exceeded, so that the algorithm will work with very small quantities of data and will produce the behavior we want. These numbers are computed separately for each microtiter plate. The probability distributions are generated using the code (written in C) attached hereto and incorporated herein by reference as Appendix A.

The Null-Class variant is used to provide genotypic class indicating No Signal.

Quality control may also be enhanced in a surprising manner using the procedures described here. In particular, the confidence score C of equation (4) serves as a robust indicator of the performance of the biochemical reaction system. For example, a downward trend in the confidence scores within a single batch or in successive batches may indicate deterioration of an important reagent or of a sample or miscalibration of the instrumentation.

Accordingly, in a preferred embodiment, the computer may be used to determine the presence of a downward trend in the confidence score over time calculated in reference to each of the following variables: the locus (is there a downward trend in the confidence score of a single locus relative to other loci tested?), the sample (is there a downward trend in the confidence score of a single sample relative to other samples tested?), plate (is there a downward trend in the confidence score of this plate relative to other plate?), and batch (relative to other batches). If a downward trend of statistical significance (using, for example a chi square test) is detected, an alarm condition is entered.

Because the confidence score is an accurate indication of the reliability of the reaction system and the genotype determination, a low confidence score associated with a given determination is taken as indicating the need for retesting.

APPENDIX A

```
/* The probability distributions in FIGS. 4, 5, 6, and 7, respectively,
   correspond to the values of xx_prob, xy_prob, yy_prob, and ns_prob, for
   all possible values of the preprocessed reaction values (x_val and
   y_val) in the range of interest (0.0 to 3.0). */
/* We assume that the following global variables are set . . . */
double x_pos_mean, x_neg_mean, y_pos_mean, y_neg_mean;
double x_val, y_val;
/* And we set the following globals . . . */
double xx_prob, xy_prob, yy_prob, ns_prob;
#define POS_VARIANCE                 0.25
#define POS_VARIANCE_INCREMENT       0.00
#define NEG_VARIANCE                 0.05
#define NEG_VARIANCE_INCREMENT       0.10
#define HET_VARIANCE                 0.10
#define HET_VARIANCE_INCREMENT       0.20
#define COND_NEG_PROB(val,given_val,val_mean) \
   normal_prob(val_mean-val,NEG_VARIANCE + NEG_VARIANCE_INCREMENT*given_val)
#define COND_HET_PROB(val,given_val) \
   normal_prob(given_val-val,HET_VARIANCE + HET_VARIANCE_INCREMENT)
double normal_prob(deviation, sigma)
double deviation, sigma;
{
   double val=exp(-(deviation*deviation)/(2.0*sigma*sigma));
   return(val>=TINY_PROB ? val : TINY_PROB);
}
void compute_probs( )
{
   double x_pos_prob, y_pos_prob, x_neg_prob, y_neg_prob;
   x_pos_prob= normal_prob((x_pos_mean-x_val),POS_VARIANCE);
   x_neg_prob= normal_prob((x_neg_mean-x_val),NEG_VARIANCE);
   y_pos_prob= normal_prob((y_pos_mean-y_val),POS_VARIANCE);
   y_neg_prob= normal_prob((y_neg_mean-y_val),NEG_VARIANCE);
   ns_prob=   max(x_neg_prob * COND_NEG_PROB(y_val,x_val,y_neg_mean),
                  y_neg_prob * COND_NEG_PROB(x_val,y_val,x_neg_mean));
   xx_prob= x_pos_prob * COND_NEG_PROB(y_val,x_val,y_neg_mean);
   yy_prob= y_pos_prob * COND_NEG_PROB(x_val,y_val,x_neg_mean);
   xy_prob=   max(x_pos_prob * COND_HET_PROB(y_val,x_val),
                  y_pos_prob * COND_HET_PROB(x_val,y_val));
}
```

What is claimed is:

1. A device for determining the genotype at a locus within genetic material obtained from a subject, the device comprising:

(a) a reaction value generator that produces a first reaction value, indicative of the presence of a given allele at the locus, the first reaction value being attributable to reaction of the material at the locus;

(b) a digital storage medium, coupled to the reaction value generator, for storing as part of a data set the first reaction value received from the reaction value generator and other reaction values obtained under comparable conditions;

(c) distribution establishment means for retrieving data in the data set, and establishing from the data a set of probability distributions, including at least one distribution, the probability distributions associating hypothetical reaction values with corresponding probabilities for each genotype of interest at the locus;

(d) genotype calculation means for calculating the conditional probability of each genotype of interest at the locus by retrieving the first reaction value from the digital storage medium and applying the first reaction value to each probability distribution in the set of probability distributions that is pertinent to the first reaction value; and (e) genotype determination means for accessing data produced from the genotype calculation means to determine the genotype.

2. A device according to claim 1, for determining the genotype at selected loci within genetic material obtained from a subject, wherein:

(i) the reaction value generator includes means for producing a physical state, quantifiable as a reaction value, indicative of the presence of a given allele at each of the selected loci;

(ii) the data set includes reaction values obtained with respect to each of the selected loci; and (iii) the genotype calculation means includes means for applying reaction values obtained with respect to each of the selected loci to each pertinent probability distribution.

3. A device according to claim 1, for determining the genotype at a locus within genetic material obtained from each of a plurality of samples, wherein:

(i) the reaction value generator includes means for producing a second physical state, quantifiable as a second reaction value, independently indicative of the presence of a second allele at the locus;

(ii) the a digital storage medium includes means for storing a second data set including the second reaction value and other reaction values obtained under comparable conditions;

(iii) the genotype calculation means includes means for applying the first and second reaction values to each pertinent probability distribution to determine a measure of the conditional probability of each genotype of interest at the locus.

4. A device according to claim 1, wherein:

(i) the reaction value generator includes means for producing a physical state, quantifiable as a reaction value, indicative of the presence of a given allele at each of the selected loci;

(ii) the data set includes reaction values obtained with respect to each of the selected loci; and (iii) the genotype calculation means includes means for applying reaction values obtained with respect to each of the selected loci to each pertinent probability distribution.

5. A device according to claim 4, wherein each probability distribution associates a hypothetical pair of first and second reaction values with a single probability of each genotype of interest.

6. A device according to claim 1, wherein the reaction value generator includes an electromagnetic energy transducer.

7. A device according to claim 3, wherein the reaction value generator includes an electromagnetic energy transducer.

8. A device according to claim 5, wherein the reaction value generator includes an electromagnetic energy transducer.

9. A device according to claim 6, wherein the locus includes a plurality of proximal nucleotides.

10. A device according to claim 6, wherein the transducer is an optical transducer.

11. A device according to claim 10, wherein the optical transducer includes means for providing a digitized image.

12. A device according to claim 3, wherein the reaction value generator includes means for determining, on a substantially concurrent basis, the reaction values with respect to each sample.

13. A device according to claim 7, wherein the reaction value generator includes means for determining, on a substantially concurrent basis, the reaction values with respect to each sample.

14. A device according to claim 1, wherein the distribution establishment means includes (a) assignment means for establishing initial probability distributions to the data set that associate hypothetical reaction values with corresponding probabilities for each genotype of interest at the locus; (b) test means for invoking the genotype calculation means to use each initial probability distribution to determine measures of initial conditional probabilities for a genotype of interest at the locus; and (c) modifying means for modifying each initial probability distribution, so that each modified distribution more accurately reflects the reaction values stored in the digital storage medium.

* * * * *